(12) United States Patent
Itoh

(10) Patent No.: US 6,451,566 B1
(45) Date of Patent: Sep. 17, 2002

(54) METHOD FOR PRODUCING DIHYDROXYACETONE-3-PHOSPHATE

(75) Inventor: Nobuya Itoh, Toyama (JP)

(73) Assignee: Daicel Chemical Industries, Inc., Osaka (JP)

( * ) Notice: Subject to any disclaimer, the term of this patent is extended or adjusted under 35 U.S.C. 154(b) by 0 days.

(21) Appl. No.: 09/367,583

(22) PCT Filed: Dec. 18, 1998

(86) PCT No.: PCT/JP98/05743

§ 371 (c)(1),
(2), (4) Date: Dec. 2, 1999

(87) PCT Pub. No.: WO99/32638

PCT Pub. Date: Jul. 1, 1999

(30) Foreign Application Priority Data

Jan. 22, 1997 (JP) .............................................. 9-352610

(51) Int. Cl.⁷ .............................. C12P 9/00; C12P 7/28; C12N 9/12; C12N 1/19; C07H 21/04
(52) U.S. Cl. ...................... 435/131; 435/148; 435/150; 435/194; 435/252.3; 435/252.33; 435/254.11; 435/320.1; 536/23.2
(58) Field of Search .......................... 435/194, 15, 148, 435/150, 131, 252.3, 252.33, 320.1, 254.11; 536/23.2

(56) References Cited

U.S. PATENT DOCUMENTS 4,579,822 A    4/1986   Itoh et al. .................... 435/194

OTHER PUBLICATIONS

Johnson et al.( Oct. 1984) J.Bacteriology, vol. 160, pp. 55–60.*

Daniel, Rolf et al., "Biochemical and Molecular Characterization of the Oxidative Branch of . . . ," Journal of Bacteriology, vol. 177, p. 4392–4401, Aug. 1995.

Kimura, Tetsuya et al., "Cloning and characterization of two genes encoding dihydroxyacetone . . . ," Biochemica et Biophysica Acta, p. 361–368, 1998.

\* cited by examiner

Primary Examiner—Elizabeth Slobodyansky
(74) Attorney, Agent, or Firm—Fish & Richardson P.C.

(57) ABSTRACT

Methods are provided to produce highly concentrated dihydroxyacetone-3-phosphate efficiently by a simple catalytic reaction of dihydroxyacetone with the bacterial cells transformed with the gene encoding a dihydroxyacetone kinase or the dihydroxyacetone kinase produced by said bacterium.

21 Claims, 1 Drawing Sheet

SEQUENCE LISTING

<160> NUMBER OF SEQ ID NOS: 4

<210> SEQ ID NO 1
<211> LENGTH: 1743
<212> TYPE: DNA
<213> ORGANISM: Schizosaccharomyces pombe
<220> FEATURE:
<221> NAME/KEY: CDS
<222> LOCATION: (1)..(1743)
<223> OTHER INFORMATION: IFO 0354

<400> SEQUENCE: 1

```
atg gat aag cac ttt atc aac gat cct gaa gtc ctc gtc ctt gat ggc      48
Met Asp Lys His Phe Ile Asn Asp Pro Glu Val Leu Val Leu Asp Gly
 1               5                  10                  15 ctt aaa tcc ttg gcc gac atg aac aaa act tta act gtt cat gaa gag      96
Leu Lys Ser Leu Ala Asp Met Asn Lys Thr Leu Thr Val His Glu Glu
             20                  25                  30 gga aaa ttc atc tat ttc cat gac tac aac aaa aag aat gtc agt gtc     144
Gly Lys Phe Ile Tyr Phe His Asp Tyr Asn Lys Lys Asn Val Ser Val
         35                  40                  45 att tcc ggc ggt ggt gct ggt cat gaa ccc act cat tct tcg ttc gtg     192
Ile Ser Gly Gly Gly Ala Gly His Glu Pro Thr His Ser Ser Phe Val
     50                  55                  60 ggc aag ggt atg ctt act gcc gcc gtc tca ggc tcc att ttt gct tct     240
Gly Lys Gly Met Leu Thr Ala Ala Val Ser Gly Ser Ile Phe Ala Ser
 65                  70                  75                  80 ccg tcg tca aag caa att tat acc ggt att aag caa gtc gaa tct gag     288
Pro Ser Ser Lys Gln Ile Tyr Thr Gly Ile Lys Gln Val Glu Ser Glu
                 85                  90                  95 gct ggc acc ttg gta att tgc aaa aac tac acc ggt gac atc ctt cac     336
Ala Gly Thr Leu Val Ile Cys Lys Asn Tyr Thr Gly Asp Ile Leu His
            100                 105                 110 ttt ggt atg gcc ttg gag aag caa aga acg gct ggt aag aag gct gaa     384
Phe Gly Met Ala Leu Glu Lys Gln Arg Thr Ala Gly Lys Lys Ala Glu
        115                 120                 125 ctt att gcc gtt gca gat gac gta tca gta ggt cgt aag aag agc ggt     432
Leu Ile Ala Val Ala Asp Asp Val Ser Val Gly Arg Lys Lys Ser Gly
    130                 135                 140 aag gtc gga cgt cgt ggt ttg tct ggt act gtt ctt gtt cac aaa atc     480
Lys Val Gly Arg Arg Gly Leu Ser Gly Thr Val Leu Val His Lys Ile
145                 150                 155                 160 gct ggt gca gct gcc gcc aga ggg tta cct ttg gaa gcc gtt acg acc     528
Ala Gly Ala Ala Ala Ala Arg Gly Leu Pro Leu Glu Ala Val Thr Thr
                165                 170                 175 att gct aag gct gct att gac aat ttg gtt agt atc ggt gct tca ctc     576
Ile Ala Lys Ala Ala Ile Asp Asn Leu Val Ser Ile Gly Ala Ser Leu
            180                 185                 190 gct cac gtt cac gtc cct ggt cat gag cca att gca aaa gaa gat gaa     624
Ala His Val His Val Pro Gly His Glu Pro Ile Ala Lys Glu Asp Glu
        195                 200                 205 atg aaa cat gat gaa atg gaa ctt gga atg ggt att cac aat gaa cct     672
Met Lys His Asp Glu Met Glu Leu Gly Met Gly Ile His Asn Glu Pro
    210                 215                 220 gga tgc aag cgt att tcc cct att ccc tct att gat gac cta att gct     720
Gly Cys Lys Arg Ile Ser Pro Ile Pro Ser Ile Asp Asp Leu Ile Ala
225                 230                 235                 240 cag atg ctt aag caa atg ttg gat caa tcc gac aag gac cgt gcc tat     768
Gln Met Leu Lys Gln Met Leu Asp Gln Ser Asp Lys Asp Arg Ala Tyr
                245                 250                 255
```

-continued

```
gta aag att gag ggt gac gat gaa gta gtc tta ctt atg aat aac ctt      816
Val Lys Ile Glu Gly Asp Asp Glu Val Val Leu Leu Met Asn Asn Leu
            260                 265                 270 ggt ggt ctt tcc atg ctt gaa ttc agt gcc att agc cac aag gtg aag      864
Gly Gly Leu Ser Met Leu Glu Phe Ser Ala Ile Ser His Lys Val Lys
                275                 280                 285 gaa gca ttg gct aaa gaa tac aaa atc aac ccc gtt cgc atc ttt gcc      912
Glu Ala Leu Ala Lys Glu Tyr Lys Ile Asn Pro Val Arg Ile Phe Ala
        290                 295                 300 ggt cca ttt acc acc agt ttg aat ggc ttg ggt ttc ggt atc act ttg      960
Gly Pro Phe Thr Thr Ser Leu Asn Gly Leu Gly Phe Gly Ile Thr Leu
305                 310                 315                 320 ctc cgt acc act gac cgc gtc aaa gtc gag ggc gaa gaa tac tct ttg     1008
Leu Arg Thr Thr Asp Arg Val Lys Val Glu Gly Glu Glu Tyr Ser Leu
                325                 330                 335 gtt gat ttg att gac caa cct gtt gaa gct atc gga tgg cct ttg tgt     1056
Val Asp Leu Ile Asp Gln Pro Val Glu Ala Ile Gly Trp Pro Leu Cys
            340                 345                 350 caa ccc tct gac ttg aag tcc aaa aac aag att ggc aat gtc agc atc     1104
Gln Pro Ser Asp Leu Lys Ser Lys Asn Lys Ile Gly Asn Val Ser Ile
        355                 360                 365 gag gag ggt cag aag gat gtc aag tct ccc gtt act gtc gat aag gag     1152
Glu Glu Gly Gln Lys Asp Val Lys Ser Pro Val Thr Val Asp Lys Glu
370                 375                 380 aag gtt cgt cag gcg att gtc aat tcg atg gag aat ctc atc aaa gca     1200
Lys Val Arg Gln Ala Ile Val Asn Ser Met Glu Asn Leu Ile Lys Ala
385                 390                 395                 400 gag cct aaa att aca aag ttc gat acg atg gct ggt gat ggt gac tgt     1248
Glu Pro Lys Ile Thr Lys Phe Asp Thr Met Ala Gly Asp Gly Asp Cys
                405                 410                 415 ggt act act ttg aag cgt ggt gct gaa ggt gtt ttg aag ttt gtt aaa     1296
Gly Thr Thr Leu Lys Arg Gly Ala Glu Gly Val Leu Lys Phe Val Lys
            420                 425                 430 tcc gac aaa ttc tct gac gat cct att cgt att gtt cgt gat atc gca     1344
Ser Asp Lys Phe Ser Asp Asp Pro Ile Arg Ile Val Arg Asp Ile Ala
        435                 440                 445 gat gtt att gaa gac aat atg gat ggt aca tct ggt gct ttg tac gcc     1392
Asp Val Ile Glu Asp Asn Met Asp Gly Thr Ser Gly Ala Leu Tyr Ala
450                 455                 460 att ttc ttc cat ggc ttt gcg aag ggc atg aaa gac acc ttg gag aag     1440
Ile Phe Phe His Gly Phe Ala Lys Gly Met Lys Asp Thr Leu Glu Lys
465                 470                 475                 480 agc aag gac att tca tct aag aca tgg gct gct ggt ttg aag gtt gct     1488
Ser Lys Asp Ile Ser Ser Lys Thr Trp Ala Ala Gly Leu Lys Val Ala
                485                 490                 495 ctt gat act ctt ttc aag tat act ccc gct cgt cct ggt gac agc act     1536
Leu Asp Thr Leu Phe Lys Tyr Thr Pro Ala Arg Pro Gly Asp Ser Thr
            500                 505                 510 atg tgt gat gct ctt gtt cca ttt gtc gaa aca ttt gtt aaa act aat     1584
Met Cys Asp Ala Leu Val Pro Phe Val Glu Thr Phe Val Lys Thr Asn
        515                 520                 525 gat ctt aat gct gcc gta gag gag gct cgt aaa ggt gct gat gct act     1632
Asp Leu Asn Ala Ala Val Glu Glu Ala Arg Lys Gly Ala Asp Ala Thr
530                 535                 540 gca gat atg caa gcc aaa ctt gga cgt gct gtc tac gtt ggt gat gat     1680
Ala Asp Met Gln Ala Lys Leu Gly Arg Ala Val Tyr Val Gly Asp Asp
545                 550                 555                 560 gtt aaa gtt ccc gat gcc ggc gct ctt ggt gtc gtt gca att gtc gaa     1728
Val Lys Val Pro Asp Ala Gly Ala Leu Gly Val Val Ala Ile Val Glu
```

```
                565           570           575
gga ttt acg aaa taa                                         1743
Gly Phe Thr Lys
        580
```

<210> SEQ ID NO 2
<211> LENGTH: 580
<212> TYPE: PRT
<213> ORGANISM: Schizosaccharomyces pombe

<400> SEQUENCE: 2

```
Met Asp Lys His Phe Ile Asn Asp Pro Glu Val Leu Val Leu Asp Gly
 1               5                  10                  15

Leu Lys Ser Leu Ala Asp Met Asn Lys Thr Leu Thr Val His Glu Glu
            20                  25                  30

Gly Lys Phe Ile Tyr Phe His Asp Tyr Asn Lys Lys Asn Val Ser Val
        35                  40                  45

Ile Ser Gly Gly Gly Ala Gly His Glu Pro Thr His Ser Ser Phe Val
    50                  55                  60

Gly Lys Gly Met Leu Thr Ala Ala Val Ser Gly Ser Ile Phe Ala Ser
65                  70                  75                  80

Pro Ser Ser Lys Gln Ile Tyr Thr Gly Ile Lys Gln Val Glu Ser Glu
                85                  90                  95

Ala Gly Thr Leu Val Ile Cys Lys Asn Tyr Thr Gly Asp Ile Leu His
            100                 105                 110

Phe Gly Met Ala Leu Glu Lys Gln Arg Thr Ala Gly Lys Lys Ala Glu
        115                 120                 125

Leu Ile Ala Val Ala Asp Asp Val Ser Val Gly Arg Lys Lys Ser Gly
    130                 135                 140

Lys Val Gly Arg Arg Gly Leu Ser Gly Thr Val Leu His Lys Ile
145                 150                 155                 160

Ala Gly Ala Ala Ala Arg Gly Leu Pro Leu Glu Ala Val Thr Thr
                165                 170                 175

Ile Ala Lys Ala Ala Ile Asp Asn Leu Val Ser Ile Gly Ala Ser Leu
            180                 185                 190

Ala His Val His Val Pro Gly His Glu Pro Ile Ala Lys Glu Asp Glu
        195                 200                 205

Met Lys His Asp Glu Met Glu Leu Gly Met Gly Ile His Asn Glu Pro
    210                 215                 220

Gly Cys Lys Arg Ile Ser Pro Ile Pro Ser Ile Asp Asp Leu Ile Ala
225                 230                 235                 240

Gln Met Leu Lys Gln Met Leu Asp Gln Ser Asp Lys Asp Arg Ala Tyr
                245                 250                 255

Val Lys Ile Glu Gly Asp Asp Glu Val Val Leu Leu Met Asn Asn Leu
            260                 265                 270

Gly Gly Leu Ser Met Leu Glu Phe Ser Ala Ile Ser His Lys Val Lys
        275                 280                 285

Glu Ala Leu Ala Lys Glu Tyr Lys Ile Asn Pro Val Arg Ile Phe Ala
    290                 295                 300

Gly Pro Phe Thr Thr Ser Leu Asn Gly Leu Gly Phe Gly Ile Thr Leu
305                 310                 315                 320

Leu Arg Thr Thr Asp Arg Val Lys Val Glu Gly Glu Glu Tyr Ser Leu
                325                 330                 335

Val Asp Leu Ile Asp Gln Pro Val Glu Ala Ile Gly Trp Pro Leu Cys
```

-continued

```
                    340                 345                 350
    Gln Pro Ser Asp Leu Lys Ser Lys Asn Lys Ile Gly Asn Val Ser Ile
                355                 360                 365

Glu Glu Gly Gln Lys Asp Val Lys Ser Pro Val Thr Val Asp Lys Glu
        370                 375                 380

Lys Val Arg Gln Ala Ile Val Asn Ser Met Glu Asn Leu Ile Lys Ala
    385                 390                 395                 400

Glu Pro Lys Ile Thr Lys Phe Asp Thr Met Ala Gly Asp Gly Asp Cys
                    405                 410                 415

Gly Thr Thr Leu Lys Arg Gly Ala Glu Gly Val Leu Lys Phe Val Lys
                420                 425                 430

Ser Asp Lys Phe Ser Asp Pro Ile Arg Ile Val Arg Asp Ile Ala
                435                 440                 445

Asp Val Ile Glu Asp Asn Met Asp Gly Thr Ser Gly Ala Leu Tyr Ala
            450                 455                 460

Ile Phe Phe His Gly Phe Ala Lys Gly Met Lys Asp Thr Leu Glu Lys
    465                 470                 475                 480

Ser Lys Asp Ile Ser Ser Lys Thr Trp Ala Ala Gly Leu Lys Val Ala
                    485                 490                 495

Leu Asp Thr Leu Phe Lys Tyr Thr Pro Ala Arg Pro Gly Asp Ser Thr
                500                 505                 510

Met Cys Asp Ala Leu Val Pro Phe Val Glu Thr Phe Val Lys Thr Asn
                515                 520                 525

Asp Leu Asn Ala Ala Val Glu Glu Ala Arg Lys Gly Ala Asp Ala Thr
                530                 535                 540

Ala Asp Met Gln Ala Lys Leu Gly Arg Ala Val Tyr Val Gly Asp Asp
    545                 550                 555                 560

Val Lys Val Pro Asp Ala Gly Ala Leu Gly Val Val Ala Ile Val Glu
                    565                 570                 575

Gly Phe Thr Lys
                580

<210> SEQ ID NO 3
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 3
gccggtacca ggagctaaaa tatggataag cac                              33

<210> SEQ ID NO 4
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 4
gccaagctta aaatttcgta tccaattatt tcg                              33
```

METHOD FOR PRODUCING DIHYDROXYACETONE-3-PHOSPHATE

TECHNICAL FIELD

The present invention relates to a method for producing dihydroxyacetone-3-phosphate using enzyme.

BACKGROUND ART

Dihydroxyacetone-3-phosphate is a substrate for fructose 1,6-bisphosphate aldolase and is used for stereoselectively synthesizing many kinds of carbohydrates by aldol condensation with various aldehydes. The carbohydrates thus synthesized can be widely utilized as medicines and their synthetic intermediates. The above reaction, however, requires large excesses of expensive dihydroxyacetone-3-phosphate, making the products expensive.

For example, dihydroxyacetone-3-phosphate can be chemically produced by directly phosphorylating dihydroxyacetone dimer with phosphorus oxychloride ($POCl_3$) in pyridine (Tetrahedron Lett., 28, 1641 (1987)). This production method is complicated and thus cannot produce dihydroxyacetone-3-phosphate in a high yield at low cost.

Methods of producing dihydroxyacetone-3-phosphate using enzymes have also been reported. An example thereof is a method of synthesizing dihydroxyacetone-3-phosphate from dihydroxyacetone with immobilized glycerol kinase (GK) under conditions that ATP is regenerated by using phosphoenolpyruvic acid and pyruvate kinase (PK) (J. Org. Chem., 48, 3199(1983), and J. Am. Chem. Soc., 107, 7019(1985)). In this method, acetate kinase and acetylphosphate may be used instead of phosphoenolpyruvic acid and pyruvate kinase (J. Am. Chem. Soc., 107, 7019(1985)). These methods using glycerol kinase (GK) require highly purified enzymes and therefore cannot produce dihydroxyacetone-3-phosphate in a high yield at low cost.

For another example, it is theoretically possible to produce dihydroxyacetone-3-phosphate from dihydroxyacetone using dihydroxyacetone kinase (DHAK) (examined published Japanese patent applications (JP-B) No. Hei 4-29349 and Hei 4-22560). In particular, dihydroxyacetone kinase derived from yeast *Schizosaccharomyces pombe* is suitable for producing dihydroxyacetone-3-phosphate (JP-B Hei 4-29349). However, the cell extract of *Schizosaccharomyces pombe* contains coexisting enzymes such as phosphatases and triose-3-phosphate isomerase, which degrade the formed dihydroxyacetone-3-phosphate. The enzyme thus needs to be highly purified and has not yet been applied practically.

For the practical production of dihydroxyacetone-3-phosphate using enzymes, the enzyme or the biocatalyst containing the enzyme should have high reactivity, be prepared easily at low cost, and be highly purified so as not to degrade the product, dihydroxyacetone-3-phosphate. No efficient method for producing dihydroxyacetone-3-phosphate by using enzymes or biocatalysts containing the enzymes, which meets the above requirements, has been developed.

DISCLOSURE OF THE INVENTION

An objective of this invention is to provide a method, for efficiently producing dihydroxyacetone-3-phosphate.

Under the above circumstances, the present inventors have attempted to clone a gene encoding dihydroxyacetone kinase and to express it efficiently to obtain the practical enzyme. The present inventors have succeeded in overexpressing the enzyme in a microbial host. Furthermore, the present inventors have found that dihydroxyacetone-3-phosphate can be produced in a high concentration by contacting the host cells as they are or the enzyme produced by them with dihydroxyacetone, the substrate of the enzyme, thereby accomplishing the present invention.

More specifically, this present invention relates to:
(1) a method for producing dihydroxyacetone-3-phosphate, which comprises contacting dihydroxyacetone with bacterial cells transformed with the gene encoding dihydroxyacetone kinase or the enzyme produced by the bacterial cells;
(2) a method described in (1), wherein said dihydroxyacetone kinase is derived from yeast belonging to the genus Schizosaccharomyces;
(3) a method described in (1), wherein said dihydroxyacetone kinase is derived from *Schizosaccharomyces pombe*;
(4) a method described in (1), wherein said bacterial cell is *Escherichia coli*; and
(5) a method described in any one of (1) to (4), wherein said contacting is performed under the conditions that coenzyme, ATP, is regenerated.

The source of the gene encoding dihydroxyacetone kinase used in the present invention is not limited. It is preferably derived from yeast belonging to the genus Schizosaccharomyces; more preferably, *Schizosaccharomyces pombe*; and still more preferably, *Schizosaccharomyces pombe* IFO 0354. The nucleotide sequence of the dihydroxyacetone kinase gene from *Schizosaccharomyces pombe* IFO 0354 is shown in SEQ ID NO: 1, and the deduced amino acid sequence is shown in SEQ ID NO: 2.

In the method of this invention, microorganisms transformed with dihydroxyacetone kinase capable of overexpressing the enzyme can be used as they are as an enzyme catalyst. The term "overexpression" as used herein means a higher level expression than spontaneous [ex]pression. In general, transformants capable of overexpresing the expression product can be obtained by introducing multiple copies of the expression unit with the gene encoding the expression product into host cells. The host bacterial cells used in the present invention are not particularly limited. It is preferable to use bacteria belonging to the genus Escherichia, and more preferable to use *E. coli* K-12 strain because various host-vector systems can be used. For example, pUC118 or pUC119 is the preferable expression vector into which the dihydroxyacetone kinase gene is to be inserted (Methods in Enzymology, 153, 3 (1987)). The gene can be introduced into the host cell by methods well known in the art such as a method described in "Methods in Enzymology, 68, 299 (1979)." For example, *E. coli* capable of overexpressing dihydroxyacetone kinase can be prepared as described below. First, the primers are designed for polymerase chain reaction (PCR) based on the database resulting from genome analysis of *Schizosaccharomyces pombe*. The target DNA is amplified by PCR using the primers and genomic DNA isolated from *Schizosaccharomyces pombe* IFO 0354 as a template DNA by conventional procedures. The PCR products are ligated into appropriate vectors and are cloned. The gene-inserted vectors are transformed into an appropriate strain of *E. coli*, and the transformants are then selected by detecting the existence of drug resistant gene(s) and the DNA insert(s). The DHAK productivity of the clones is measured by assaying the activity of the enzyme.

The enzyme produced by the bacterial cells can be isolated from the cells for use in the method of the present invention. The enzyme is not necessarily purified. A crude enzyme is used as well as the purified enzyme. The dihydroxyacetone kinase can be recovered from the grown cells by extracting the enzyme from the cells first because the enzyme is produced intracellularly. Namely, the cells are collected from the culture medium by filtration or centrifugation and disrupted by mechanical methods such as treatment with alumina, dynomill, or ultrasonication to extract the enzyme in a soluble form. Alternatively, the cell membranes are destroyed by treatment with organic solvents such as acetone, and the resulting cells are dried under reduced pressure. The powder thus prepared is used as a catalyst containing the enzyme. Insoluble materials are removed from the culture obtained in the methods described above by filtration or centrifugation to obtain the crude enzyme. Furthermore, the crude enzyme is concentrated and purified by methods known in the art such as adsorption chromatography, ion exchange chromatography, and gel filtration chromatography. The thus-obtained, partially purified preparation of dihydroxyacetone kinase is also used in the method of this invention.

The dihydroxyacetone kinase activity of the *E. coli* strain that overexpresses the enzyme or the enzyme isolated from said cells is measured by known methods (JP-B Hei 04-29349) as follows. The decrease of absorbance at 340 nm is spectrophotometrically measured during the reaction at 25° C. in 1 ml of the reaction mixture containing 0.1M triethanolamine buffer (pH 7.5), 2.5 mM ATP, 4 mM $MgSO_4$, 0.2 mM NADH, 2.5 units of glycerol-3-phosphate dehydrogenase (G3PDH), and 0.01 ml of a test enzyme solution (formula below).

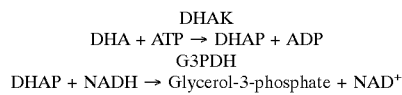

One unit of the enzyme of the present invention is defined as the amount required to decrease 1 μmole of NADH in 1 min under the conditions described above.

Dihydroxyacetone-3-phosphate is usually produced by the method of this invention under the following conditions. First, the reaction is carried out in a buffer with pH ranging from 7 to 8. Any buffer solution can be used as long as it can keep its pH within the above reaction pH range. Tris-hydrochloride buffer is preferable. The reaction temperature may be any range as long as dihydroxyacetone kinase used is active. Preferably, the temperature ranges from about 20° C. to about 35° C. It is necessary to add ATP to the reaction mixture since dihydroxyacetone kinase requires ATP as a coenzyme. However, the enzyme is inhibited by the formed ADP. Therefore, the reaction is preferably performed with regenerating ATP. Any known systems for regenerating ATP (J. Org. Chem. 48, 3199 (1983) and J. Am. Chem. Soc. 111, 627 (1989)) can be used. In view of the production cost, a system using acetyl phosphate and acetate kinase is preferred.

Dihydroxyacetone-3-phosphate produced by the above reaction can be identified by enzymatic and chemical techniques. Namely, the decrease of absorbance at 340 nm is spectrophotometrically measured during the reaction (formula below) at 30° C. in 3 ml of a reaction mixture containing 0.1 M sodium acetate buffer (pH 6.0), 0.25 mM NADH, 0.6 units of glycerol-3-phosphate dehydrogenase (G3PDH), and 0.01 ml of a test solution. The concentration of dihydroxyacetone-3-phosphate (DHA phosphate) in the test solution is then determined based on a calibration curve which is made in advance using the standard compound.

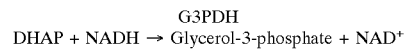

After the above reaction, the reaction product can be precipitated by adding organic solvents such as ethanol to the reaction mixture, or by salting out, to recover it. Furthermore, the reaction product is purified by usual purification procedures such as column chromatography and recrystallization. Alternatively, it can be subjected to the next procedure as it is.

BEST MODE FOR IMPLEMENTING THE INVENTION

Figure 1:
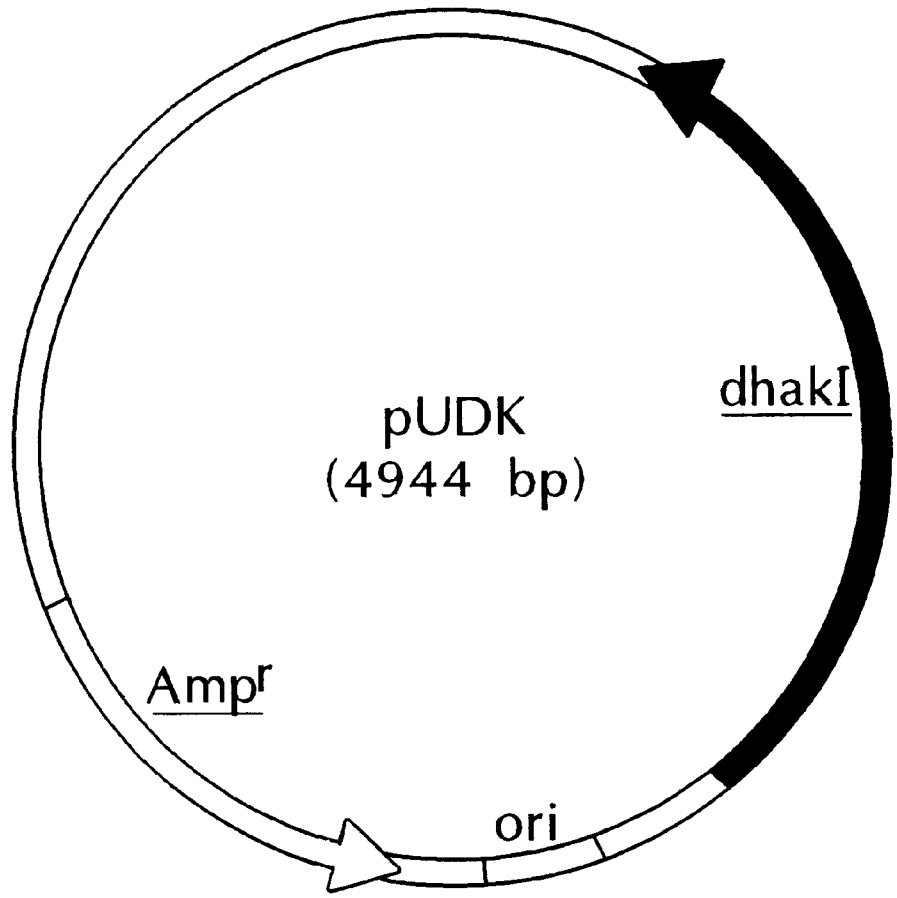
FIG. 1 illustrates the structure of the pUDK vector.

The following examples illustrate the present invention in more detail, but are not to be construed to limit the scope of the present invention.

EXAMPLE 1

Preparing *Escherichia coli* Strain Overexpressing Dihydroxyacetone Kinase

The DHAK gene derived from *Schizosaccharomyces pombe* IFO 0354 was obtained and analyzed in the following manner. Two primers, primer A (5'-GCCGGTACCAGGAGCTAAAATATGGATAAGCAC-3', SEQ ID NO: 3) and primer B (5'-GCCAAGCTTAAAATTTCGTATCCAATTATTCG-3', SEQ ID NO: 4) were designed based on the database resulting from the genome analysis of *Schizosaccharomyces pombe*. Primer A contains the restriction endonuclease KpnI recognition site and *E. coli* SD sequence, while primer B contains the restriction endonuclease HindIII recognition site. The target gene (dhakI) was amplified by PCR using genomic DNA isolated from *Schizosaccharomyces pombe* IFO 0354 by a conventional method as a template DNA and the above primers. The PCR products were ligated with pT7BlueT vectors and cloned. The coding region of the desired gene was then isolated from the vector, and ligated with pUC118 vector. The vector thus obtained was named pUDK.

*E. coli* strain JM109 was transformed with pUDK. The transformant thus obtained was named "*E. coli* JM109 (pUDK)." Dihydroxyacetone kinase was produced by this transformant as follows. *E. coli* JM109 (pUDK) was inoculated into LB broth (1% tryptone, 0.5% yeast extract, 1% NaCl, pH 7.0) containing 100 mg/ml of ampicillin, 0.4 mm IPTG (isopropylthiogalactopyranoside) as an inducer and cultured at 37° C. for 16 hours with shaking. FIG. 1 shows the structure of the pUDK vector. SEQ ID NO: 1 shows the nucleotide sequence of dhakI, and SEQ ID NO: 2 shows the deduced amino acid sequence. The molecular weight of this enzyme was estimated to be 145,000 by an HPLC analysis, and the molecular weight of the subunit was estimated to be 63,000 by SDS-polyacrylamide gel electrophoresis. The molecular weight of the subunit agreed well with the molecular weight (62,245) of the deduced amino acid sequence. The requirement of divalent metal cations on the enzyme activity was investigated. The relative activity of the enzyme in the presence of $Ca^{2+}$, $Co^{2+}$, and $Mn^{2+}$ is 116%, 20%, and 12%, respectively, taking the relative activity of the enzyme in the presence of $Mg^{2+}$ as 100%. These results indicate that this enzyme is dimeric and that the cloned dhakI gene encodes the isozyme of dihydroxyacetone kinase I derived from *Schizosaccharomyces pombe* (JP-B Hei 04-29349).

EXAMPLE 2

Comparison of the Activities of Crude Enzyme Solutions Derived from *E. coli* JM109 (pUDK) and *S. Pombe*

*E. coli* JM109 (pUDK) was inoculated into LB broth (1% trypton, 0.5% yeast extract, 1% NaCl, pH7.0) containing 0.4 mM IPTG (isopropylthiogalactoside) and cultured at 37° C. for 16 hours with shaking. The cells were collected from the culture medium by centrifugation and resuspended in a buffer solution. The suspended cells were disrupted by sonication, and the lysate was then centrifuged to obtain the supernatant as a crude enzyme solution. *Schizosaccharomyces pombe* IFO 0354 was cultured according to the method described in JP-B Hei 04-29349, and the collected cells were disrupted by aluminum oxide to obtain the crude enzyme solution in the same manner as above. The activities (unit/dl of broth) of dihydroxyacetone kinases and contaminating enzymes from both strains are shown in Table 1.

TABLE 1

|  | *E. coli* JM109 (pUDK) | *Schizosaccharomyces pombe* IFO 0354 |
| --- | --- | --- |
| DHAK | 80 | 14 |
| alkaline phosphatase | 0 | 2.2 |
| triose-3-phoshate isomerase | 58 | 485 |

As clearly shown in Table 1, the crude enzyme solution from *E. coli* JM109 (pUDK) has high dihydroxyacetone kinase activity and low activities of contaminating enzymes, while the crude enzyme solution from *S. pombe* IFO 0354 has low dihydroxy kinase activity and high activities of contaminating enzymes. The productivity of dihydroxyactone-3-phosphate using the crude enzyme solution from both strains was measured by allowing 10 ml of a reaction mixture containing 100 mM DHA, 10 mM $MgSO_4$, 4 mM ATP, 100 mM acetyl phosphate (AcOP), 6 units of AK (Unitika Co., Ltd), 6 units of DHAK, and 0.1M Tris-HCl buffer (pH 7.3) to react at 25° C. for 10 to 15 hours. As a result, a significant difference was observed in the two. The results are shown in Table 2.

TABLE 2

|  | DHAK concentration (mM) | |
| --- | --- | --- |
| Time (hours) | *E.coli* JM109 (pUDK) | *S. pombe* IFO 0354 |
| 0 | 0 | 0 |
| 1 | 32 | 7 |
| 2 | 41 | 4 |
| 4 | 63 | 4 |
| 6 | 70 | 4 |
| 8 | 63 | 3 |
| 24 | 55 | 4 |

EXAMPLE 3

Producing Dihydroxyacetone-3-phosphate Using a Crude Enzyme Solution from *E. coli* JM109 (pUDK)

Ten milliliters of a reaction mixture containing 50 mM DHA, 10 mM $MgSO_4$, 60 mM ATP, 6 units of dihydroxyacetone kinase, and 0.1 M Tris-HCl buffer (pH 7.3) was allowed to react at 25° C. for 10 to 20 hours to produce 20 mM DHA phosphate (3.8 mg/ml of monosodium dihydroxyacetone-3-phosphate).

EXAMPLE 4

Producing Dihydroxyacetone-3-phosphate Using a Crude Enzyme Solution from *E. coli* JM109 (pUDK) with an ATP Regeneration System Ten milliliters of a reaction mixture containing 100 mM DHA, 10 mM $MgSO_4$, 4 mM ATP, 100 mM acetyl phosphate (AcOP), 6 units of AK (Unitika Co., Ltd), 6 units of a crude DHAK solution, and 0.1M Tris-HCl buffer (pH 7.3) was allowed to react at 25° C. for 10 to 15 hours, producing 70 mM DHA phosphate (13.3 mg/ml of monosodium dihydroxyacetone-3-phosphate).

EXAMPLE 5

Producing Dihydroxyacetone-3-phosphate Using *E. coli* JM109 (pUDK) with an ATP Regeneration System The reaction was performed in the same manner as in Example 2 except for using *E. coli* JM109 (PUDK) cells containing 6 units of dihydroxyacetone kinase and produced 73 mM DHA phosphate (13.9 mg/ml of monosodium dihydroxyacetone-3-phosphate).

EXAMPLE 6

Ten milliliters of a reaction mixture containing 200 mM DHA, 10 mM $MgSO_4$, 4 mM ATP, 250 mM acetyl phosphate (AcOP), 24 units of AK (Unitika Co., Ltd), 24 units of a crude DHAK solution, and 0.1 M Tris-HCl buffer (pH 7.3) was allowed to react at 25° C. for 15 to 20 hours while controlling the pH; 140 mM DHA phosphate (26.6 mg/ml as monosodium dihydroxyacetone-3-phosphate) was then produced. The time course of the reaction is shown in Table 3.

TABLE 3

| Time (hours) | DHAP concentration (mM) |
| --- | --- |
| 0 | 0 |
| 1 | 35 |
| 2 | 57 |
| 4 | 81 |
| 6 | 102 |
| 8 | 116 |
| 10 | 133 |
| 12 | 140 |
| 24 | 116 |

The reaction mixture was treated with active carbon and filtrated. Barium acetate (0.08 g) was then added to the filtrate, and the resulting precipitate was removed by filtration. The filtrate was concentrated to 3 ml under reduced pressure, then a five-fold volume of cold ethanol was added to the filtrate. The resulting precipitate was filtered and dried under reduced pressure to obtain 180 mg of monosodium dihydroxyacetone-3-phosphate.

INDUSTRIAL APPLICABILITY

The present invention provides a method for efficiently producing dihydroxyacetone-3-phosphate in a high concentration by using the enzymatic reaction of dihydroxyacetone kinase.

What is claimed is:

1. A method for producing dihydroxyacetone-3-phosphate, the method comprising contacting dihydroxyacetone with (a) a bacterial cell (1) transformed with a nucleic acid sequence encoding a dihydroxyacetone kinase comprising the amino acid sequence set forth in SEQ ID NO:2 and (2) producing said kinase, or (b) an extract of said bacterial cell.

2. A method according to claim 1, wherein said dihydroxyacetone kinase consists of the amino acid sequence set forth in SEQ ID NO:2.

3. A method according to claim 1, wherein said nucleic acid sequence comprises the sequence set forth in SEQ ID NO:1.

4. A method according to claim 1, wherein said bacterial cell is an *Escherichia coli* cell.

5. A method according to claim 1, wherein the contacting is carried-out in the presence of a regeneration system for ATP.

6. A bacterial cell (1) transformed with a nucleic acid sequence encoding a dihydroxyacetone kinase comprising the amino acid sequence set forth in SEQ ID NO:2 and (2) producing said kinase.

7. The bacterial cell of claim 6, wherein said dihydroxyacetone kinase consists of the amino acid sequence of SEQ ID NO:2.

8. The bacterial cell of claim 6, wherein said nucleic acid sequence comprises the nucleotide sequence of SEQ ID NO:1.

9. A bacterial cell lysate comprising a dihydroxyacetone kinase comprising the amino acid sequence set forth in SEQ ID NO:2.

10. The lysate of claim 9, wherein the dihydroxyacetone kinase consists of the amino acid sequence of SEQ ID NO:2.

11. An isolated nucleic acid comprising the sequence of SEQ ID NO: 1, or a degenerate variant of SEQ ID NO:1.

12. A vector containing the nucleic acid of claim 11.

13. A host cell containing the vector of claim 12.

14. The host cell of claim 13, wherein the host cell is a bacterial cell.

15. An isolated nucleic acid comprising the sequence of SEQ ID NO:1.

16. A vector containing the nucleic acid of claim 15.

17. A host cell containing the vector of claim 16.

18. The host cell of claim 17, wherein the cell is a bacterial cell.

19. The method of claim 1, wherein the dihydroxyacetone kinase is a *Schizosaccharomyces pombe* dihydroxyacetone kinase.

20. The bacterial cell of claim 6, wherein the dihydroxyacetone kinase is a *Schizosaccharomyces pombe* dihydroxyacetone kinase.

21. The bacterial lysate of claim 9, wherein the dihydroxyacetone kinase is a *Schizosaccharomyces pombe* dihydroxyacetone kinase.

* * * * *

UNITED STATES PATENT AND TRADEMARK OFFICE
CERTIFICATE OF CORRECTION

PATENT NO. : 6,451,566 B1
DATED : September 17, 2002
INVENTOR(S) : Nobuya Ito

It is certified that error appears in the above-identified patent and that said Letters Patent is hereby corrected as shown below:

<u>Title page,</u>
Item [30], Foreign Patent Application Priority Data, delete "Jan. 22, 1997" and replace with -- Dec. 22, 1997 --.

Signed and Sealed this

Eleventh Day of February, 2003

JAMES E. ROGAN
*Director of the United States Patent and Trademark Office*